United States Patent [19]
Ito

[11] Patent Number: 4,502,766
[45] Date of Patent: Mar. 5, 1985

[54] EYE INSPECTION APPARATUS WITH VARIABLE FIELD ANGLE

[75] Inventor: Yuji Ito, Kanagawa, Japan

[73] Assignee: Canon Kabushiki Kaisha, Tokyo, Japan

[21] Appl. No.: 625,184

[22] Filed: Jun. 27, 1984

Related U.S. Application Data

[63] Continuation of Ser. No. 288,780, Jul. 31, 1981, abandoned, which is a continuation of Ser. No. 030,959, Apr. 17, 1979, abandoned.

[30] Foreign Application Priority Data

Apr. 19, 1978 [JP] Japan .................. 53-47083
Apr. 26, 1978 [JP] Japan .................. 53-49618

[51] Int. Cl.³ .................. A61B 3/14; G03B 29/00
[52] U.S. Cl. .................. 351/206; 354/62
[58] Field of Search .............. 351/205, 206, 207, 208, 351/214, 221; 354/62; 350/415

[56] References Cited

U.S. PATENT DOCUMENTS

| | | | |
|---|---|---|---|
| 3,535,027 | 10/1970 | Littmann et al. | 351/16 X |
| 3,914,032 | 10/1975 | Takano et al. | 351/7 |
| 4,062,623 | 12/1977 | Suzuki et al. | 350/419 |
| 4,208,107 | 6/1980 | Oharek | 351/7 |

FOREIGN PATENT DOCUMENTS 1260923  1/1972  United Kingdom ............... 350/419

*Primary Examiner*—Rodney B. Bovernick
*Attorney, Agent, or Firm*—Toren, McGeady and Stanger

[57] ABSTRACT

An eye inspection apparatus in which an objective, an apertured mirror, a diaphragm, a fixed lens group, a compensation lens group, a variation lens group, a convergent lens group, a quick-return mirror and a photographic film are arranged in order stated with the first mentioned element nearest the eye to be inspected. In addition an observation light source, a photographic flash tube, a condenser lens, and a relay lens are directed to the aperture mirror, and further a view finder is arranged to be directed to the quick-return mirror.

22 Claims, 6 Drawing Figures

U.S. Patent   Mar. 5, 1985   Sheet 3 of 3   4,502,766

EYE INSPECTION APPARATUS WITH VARIABLE FIELD ANGLE

This is a continuation of application Ser. No. 288,780, filed July 31, 1981, which was a continuation of application Ser. No. 030,959, filed Apr. 17, 1979, both now abandoned.

BACKGROUND OF THE INVENTION

The present invention relates to an optical inspection apparatus, and particularly such apparatus which can observe or photograph the object to be inspected with variable magnification.

Eye inspections are currently conducted widely as one means of diagnosis for disease prevention, and photographs of the eye fundus provide useful informations. Multiple photographs have increasingly been utilized for the above purpose. Under this situation demands have been increasing for development of a wide angle camera for the inspection of an eye fundus which can cover a wider photographic field, thereby requiring less photographs for inspecting patients who are diagnosed. On the other hand, demands have been increasing for development of an eye fundus camera which can take an enlarged photograph with a narrow field angle. In order to meet with the above demands for two different types of camera, an apparatus has been proposed and known, in which the objective lens in the optical system of an eye fundus camera is interchanged so as to enable both the wide angle photography and the narrow angle photography. However, this conventionally known apparatus requires considerable time and effort for interchanging the objective lens, and at each time of the interchange, it is required to align of the optical axis between the eye to be inspected and the objective lens, to adjust the operative distance, and to focus again.

SUMMARY OF THE INVENTION

One of the objects of the present invention is to observe or photograph a particular portion to be inspected with varied magnification.

A second object of the present invention is to quickly enlarge or reduce the field of view.

A third object of the present invention is to change the field of view in a ocntinuous manner.

A fourth object of the present invention is to obtain a satisfactory image quality irrespective of magnification.

A fifth object of the present invention is to enable variation of magnification without increasing the total length of the apparatus as compared a retinal camera with a constant magnification.

Therefore, the present invention comprises an objective optical system opposite an eye to be inspected, a diaphragm behind the objective optical system, an image forming optical system including a lens group which moves at the time of variation of magnification, arranged at a position behind the diaphragm, and an illumination system for illuminating the portion to be inspected. The term "behind" used hereinabove means the direction away from the eye to be inspected. For achieving the subordinate objects of the present invention the system composed of the diaphragm and the image forming optical system is formed into a telecentric optical system on a wider angle side of the variable magnification range.

DESCRIPTION OF PREFERRED EMBODIMENTS

The present invention will be clearly understood from the following description of the embodiments with reference to the attached drawings.

Figure 1:
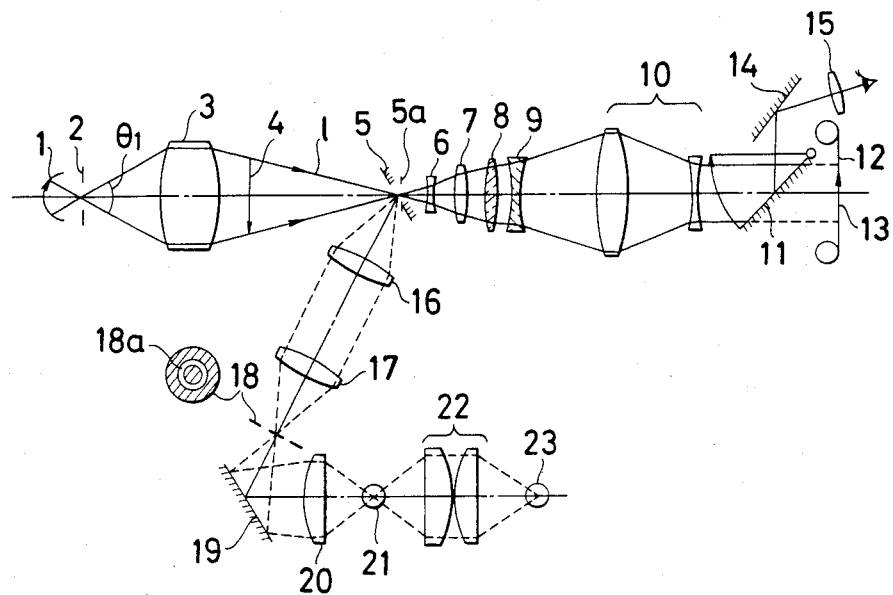
FIG. 1 shows a cross section of an embodiment of the present invention at a wider picture angle.
Figure 2:
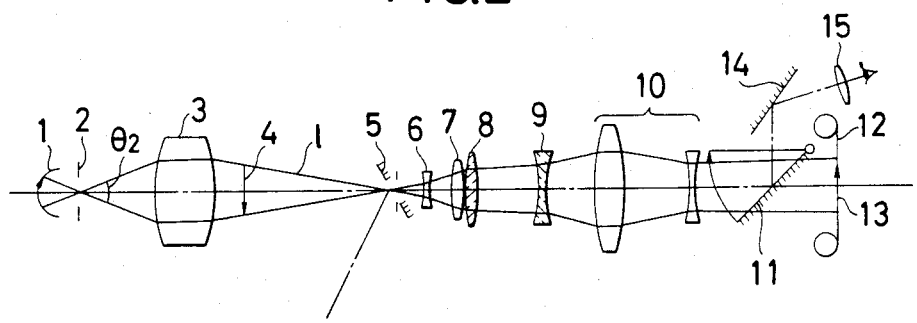
FIG. 2 shows a cross section of the embodiment at an intermediate picture angle.
Figure 3:
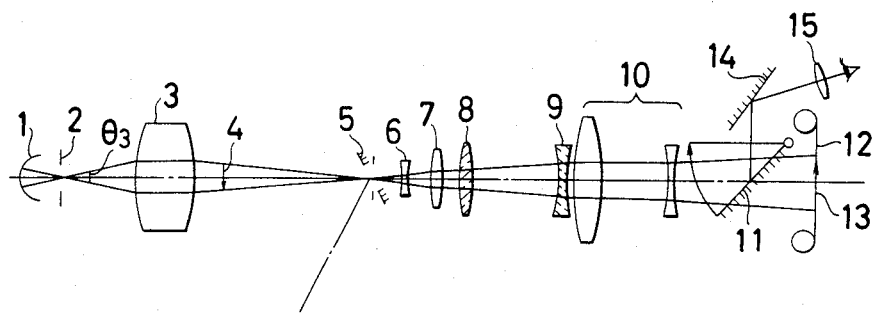
FIG. 3 shows a cross section of the embodiment at a narrow angle.

In FIGS. 1, 2 and 3 are cross sections of an embodiment according to the present invention at a wide angle, an intermediate angle and a narrow angle. The eye 1, 2 to be inspected is shown schematically. The eye is represented by the fundus 1 and the eye pupil 2. The objective lens 3 of the eye fundus camera forms a primary image 4 of the eye fundus. A reflection mirror 5 has an opening at the center. This central opening functions as a diaphragm, but a diaphragm 5a may be provided behind the reflection mirror. The diaphragm is conjugate to the eye pupil 2 or the eye diaphragm. A movable lens 6 having a negative power is moved back and forth at the time of focusing. A fixed lens 7 preceeds lenses 8 and 9, which are moved at the time of zooming simultaneously but independently from each other. A positive relay lens group 10 precedes a tiltable mirror 11, which is slanted at the time of observation and withdrawn from the optical path at the time of photographing. A photographic film 12 intercepts a final image 13 of the eye fundus, which is reformed by the image forming lens composed of the lenses 6 to 10. A conversion mirror 14 alters the optical path, and precedes an eyepiece 15, forming a finder optical system. The light beam in the solid line represents the main light beam.

Regarding the illumination system, the reflection mirror 5 having an opening is slanted to the optical axis of the objective lens 3 so as to direct the illumination light toward the objective lens 3. Component lenses 16 and 17 of the relay lens precede a light shielding plate 18 having a ring-shaped slit 18a. The next members of the illumination light path are an optical path conversion mirror 19, a condenser lens 20, a photographing light source 21, a condenser 22 and an observation light source 23. The light sources 21 and 23 are conjugate with respect to the condenser lens 22, and the shielding plate 18 and the light source 21 are conjugate with respect to the condenser lens 20. The reflection mirror 5 and the shielding plate 18 are almost conjugate with respect to the relay lens groups 16 and 17, and the reflection mirror 5 is conjugate to the eye pupil 2 or the eye diaphragm. The ring illumination and its various modifications using a light shielding plate with a ring-shaped slit are well known.

Hereinbelow the zoom lens with a diaphragm in the front will be described in detail.

As mentioned before, the lens 6 is a lens for focusing. However, this lens 6 can be omitted in certain fundus cameras in which the focusing is effected by moving the tiltable mirror, the film and the finder back and forth as a unit. The fixed lens 7 is important for correction of aberrations, and the function of this lens cannot be replaced by other lenses or lens groups. Thus, this lens 7 functions to correct the aberrations of the primary image and has correcting function for restricting variation of the aberration accompanying the variation of magnification. Thus, it is possible to improve the image quality degraded by the simple-structured objective lens and to restrict the variation of aberration caused when the movable lens moves, simply by designing the lens while taking into consideration the above corrections. Therefore, when the zooming system in this embodiment is applied, it is preferable to use the fixed lens 7 composed of two or more element lenses.

Now the significance of the aberration correction of the lens 7 in the zoom system will be explained by comparison with the aberration correction of an ordinary zoom lens. The ordinary zoom lens is composed of a focusing lens, a variator, a compensator, a diaphragm and a relay lens. The amount of the variation of aberration in each of zooming state (wide angle, intermediate angle and narrow angle) is corrected by changing the shape, the refractive index and the Abbe number of each element of the three basic groups of the focusing lens, the variator and the compensator. Thus the correction is performed not by reducing the absolute amount of aberration at each zooming state, but by reducing the difference between the zooming states. Then, in order to reduce the absolute amount of the aberration, the aberration correction is effected by using the relay lens. This procedure is possible because the photographing diaphragm is positioned between the compensator and the relay lens, and the main light beam emitted from the compensator passes through the relay lens in an almost same condition irrespective of the zooming states.

According to the embodiment of the present invention, the position at which the main light beam passes is considerably changed, as clearly illustrated by the behavior of the main light beam through in the relay lens 10 shown in FIGS. 1-3. For this reason, the fixed lens group is positioned near the diaphragm to provide abberation correction similar to that of an ordinary zoom lens. Meanwhile, the positions of the lens 6 and the lens 7 are interchangeable.

The lenses 8 and 9 which are movable at the time of zooming and the lens 9 having a negative power change the focal distance while the lens 8 having a positive power compensates for the movement of the image plane. For this purpose the absolute focal distance of the lens 8 is larger than that of the lens 9. However, the lens group 8 may have a negative power.

The relay lens group 10 is formed in a telephoto type so as to use the system composed of the diaphragm and the image forming lens as a telecentric optical system at a wide angle, for example. Therefore, at the wide angle shown in FIG. 1 the main light beam 1 is incident perpendicularly on the image forming plane (film surface).

As shown in FIGS. 1-3 and as understood from the positions at which the main light beams 1 from the lens 9 pass, the position at which the light beam enters the first lens surface of the relay lens group 10 is highest at the wide angle. Therefore, if the main light beam is simply turned in order to satisfy a precondition that the main light beam should fall on the image forming plane at the same position, the diameter of the light beam passing through the tiltable mirror 11 is remarkably increased, thus requiring an increased size of this portion.

Now, in order to avoid this disadvantage, it may be considered to weaken the convergency of the light beam and at the same time to increase the distance between the relay lens and the tiltable mirror, but this also increases the total length of the camera. Therefore, if the main light beam is maintained nearly perpendicular, it is possible to avoid the increase in the length of the mechanism and to reduce the total length of the camera.

Meanwhile, at the narrow angle in the embodiment, there is no problem because the main light beam falls on the film upwardly.

Figure 4:
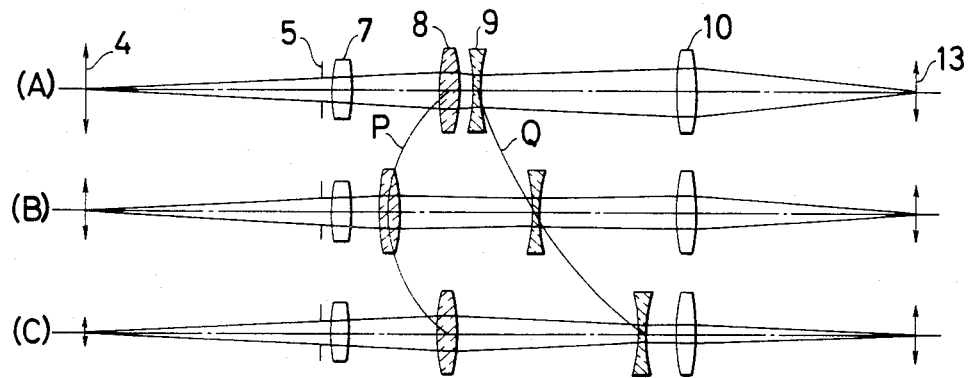
FIGS. 4A-4C respectively illustrate the zooming types of the embodiment.

As the lens 8 makes a forward convex reciprocating movement while the lens group 9 moves backward, according to the curves P and Q shown in FIGS. 4 (A), (B) and (C) so that the picture angle is successively decreased as $\theta_1 > \theta_2 > \theta_3$, while the magnification is successively increased.

For taking a photograph using the apparatus of the present invention, the observation light source 23 is illuminated to emit a light beam which passes through the condenser lenses 22 and 20 and illuminates the light shielding plate 18. The light beam coming out of the annular aperture of the light shielding plate is once converged on the reflecting mirror 5 by the relay lens groups 16 and 17, and reflected thereon.

Then, the reflection light forms on image of the annular aperture near the eye pupil 2 by the objective lens 3 and illuminates the eye fundus 1 uniformly. Of the light beams scattered by the eye fundus, the light beam, which has passed the central zone of the image of the light shielding plate formed near the eye pupil, passes through the objective lens 3, the diaphragm, the lenses or lens groups 6 to 10, and is reflected by the tiltable mirror 11 to form an image, which is observed through the eyepiece 15 and the mirror 14. For focusing, the photographing system is set at the narrow angle and the lens 6 is finely moved so as to focus the eye fundus, thereby utilizing the advantage that the depth of field becomes shallow, and achieving an accurate focusing.

Then, the picture angle is set at a desired value, the observation light source 23 is turned off and the photographing light source 21 is turned on, and tiltable mirror 11 is rapidly moved up to open the shutter (not shown), thereby exposing the film 12 with the light beam reflected by the eye fundus.

In this lens system, the fixed lens 7 is a single lens composed of the negative and positive lenses cemented together in order to shorten the whole length of the lens system.

Further the lens surface of this cemented lens has its concave surface directed toward the image, and large differences in the refractive index and the Abbe number are provided between the negative and positive lenses. Thus, the Abbe number $\nu A$ of the negative lens and the Abbe number $\nu B$ of the positive lens are preferably defined as $\nu B - \nu A > 30$, and the refractive index NA of the negative lens and the refractive index NB of the positive lens are preferably defined as $NA - NB > 0.15$. Thereby it is possible to relieve the astigmatism of the objective lens as well as the longitudinal and lateral chromatic aberration on axis and due to the magnification of the objective lens. It is also possible to perform a function corresponding to the aberration correction of the relay section of an ordinary zoom lens as mentioned hereinbefore.

Figure 5:
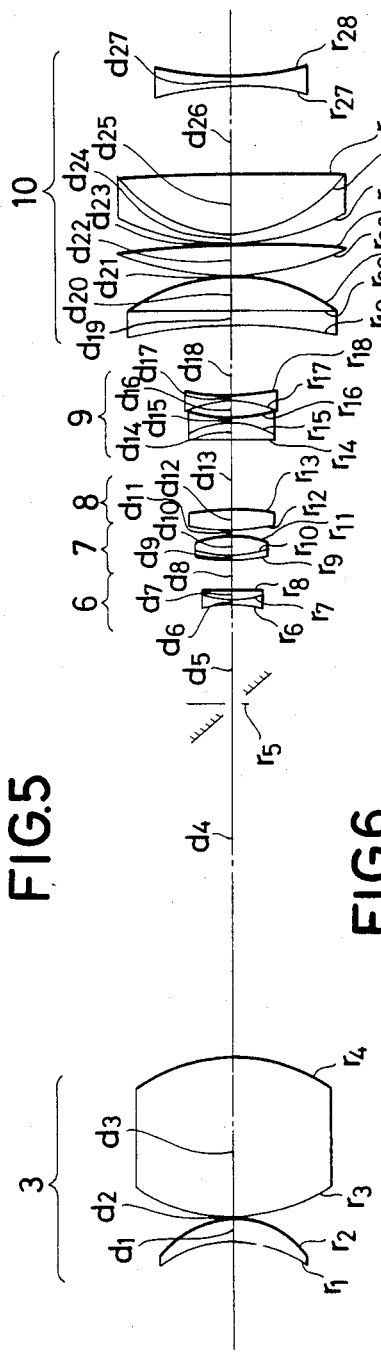
FIG. 5 shows a cross section of a lens system corresponding to the lens data shown in Table 1.

The numerical data for the lens system shown in FIG. 5 are set forth in Table 1 (data for illumination system are omitted).

TABLE 1

| Surface No. | r | d | Nd | νd |
|---|---|---|---|---|
| 1 | −45.20 | 7.52 | 1.51633 | 64.1 |
| 2 | −31.76 | 0.30 | | |
| 3 | 52.86 | 51.86 | 1.56873 | 63.1 |
| 4 | −52.86* | 117.23 | | |
| 5 | diaphragm | 33.8 | | |
| 6 | −54.0 | 1.3 | 1.60738 | 56.8 |
| 7 | 35.0 | 3.5 | 1.72342 | 38.0 |
| 8 | 623.9 | 10.0 | | |
| 9 | 92.9 | 1.7 | 1.80518 | 25.4 |
| 10 | 39.5 | 6.0 | 1.48749 | 70.1 |
| 11 | −38.7 | $d_{11}$ | | |
| 12 | 80.3 | 6.6 | 1.60311 | 60.7 |
| 13 | −126.2 | $d_{13}$ | | |
| 14 | −300.3 | 5.2 | 1.75520 | 27.5 |
| 15 | −29.5 | 1.4 | 1.61700 | 62.8 |
| 16 | 68.6 | 5.4 | | |
| 17 | −39.5 | 1.4 | 1.72916 | 54.7 |
| 18 | 107.3 | $d_{18}$ | | |
| 19 | −200.4 | 2.5 | 1.75520 | 27.5 |
| 20 | 786.8 | 13.2 | 1.77250 | 49.6 |
| 21 | −62.5 | 0.3 | | |
| 22 | 106.7 | 10.2 | 1.61700 | 62.8 |
| 23 | −449.5 | 0.3 | | |
| 24 | 87.0 | 3.1 | 1.80518 | 25.4 |
| 25 | 47.8 | 19.2 | 1.61700 | 62.8 |
| 26 | −1769.8 | 29.2 | | |
| 27 | −112.6 | 3.4 | 1.75520 | 27.5 |
| 28 | 133.7 | | | |
| f | 28.6 | 49.6 | 85.9 | |
| $d_{11}$ | 10.9 | 1.6 | 10.9 | |
| $d_{13}$ | 1.4 | 23.4 | 36.1 | |
| $d_{18}$ | 35.4 | 22.7 | 0.7 | |

*aspherical

Figure 6:
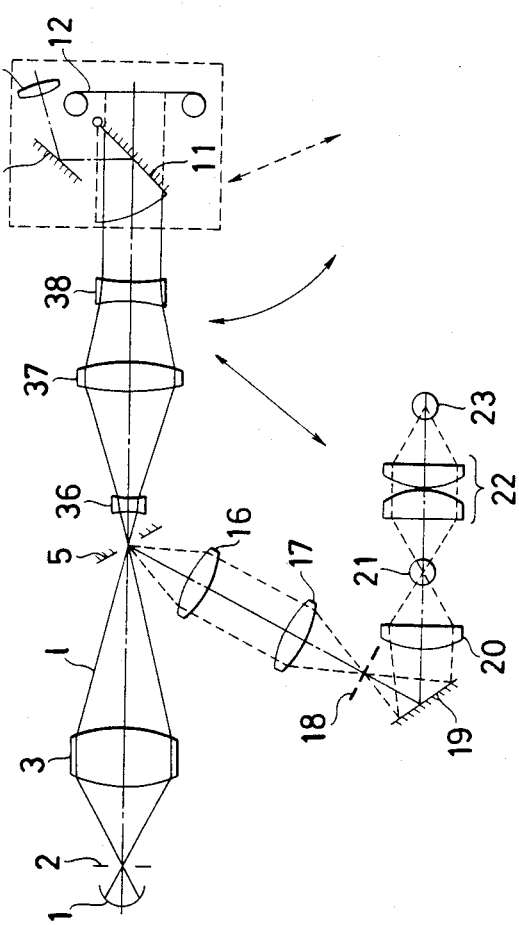
FIG. 6 shows a cross section of another embodiment of the present invention.

Another embodiment of the present invention is shown in FIG. 6 in which the same numerical references are used to represent the same members as in FIG. 1. The negative lens 36 for focusing precedes lenses 37, 38 a lens of which is moved simultaneously but independently at the time of zooming, the lens 37 having a positive power and functioning mainly to compensate the movement of the image plane, and the lens 38 having a negative power and functioning mainly to change the focal distance. The system composed of the diaphragm 5, the lenses 36, 37 and 38 constitute a telecentric optical system at the wide angle to shorten the whole length of the system.

At the time of zooming, the lens 37 is linearly moved toward the eyes being inspected, while the lens 38 is non-linearly moved and the system deviates out of the telecentric optical system as the picture angle becomes narrow.

As described above, the zooming is made possible by moving the lens 37 and 38, and further it is possible to increase the rate of variation of the magnification by making the mirror 11, the film 12, the mirror 14 and the eyepiece 15 movable all together in the direction of the optical axis. Thus, as the picture angle becomes narrower, the film 12 moves further from the eye being inspected. By moving the film and the lens groups, the magnification is increased, and by decreasing the moving amount of the lens groups, the increase in the total length of the lens system is avoided, and at the same time it is possible to reduce the size of the lens groups by the reduction of the diameter of the incident light beam which is achieved by decreasing the amount of movement.

According to the present invention as described above, it is possible to quickly perform operations such as observation of the object to be inspected, enlarged observation of any detected symptom, and enlarged photographing. Further in the present invention, as the variation of magnification is performed in connection with the primary image of the objective lens and subsequent images, so that it is not necessary to adjust the alignment even when the picture angle is changed, and as it is possible to maintain the focusing condition during the variation of magnification, it is possible to perform observation and photographing of one patient at the wide angle and at the narrow angle sequentially.

Also as described in connection with the embodiment, when the focusing is performed with the photographing system adjusted to the narrow angle, thus utilizing the performance inherent to the zoom lens, a narrow depth of field can be achieved so that it is possible to obtain more accurate adjustment of the focal point.

Further in a fundus camera in general, when the alignment between the eye to be inspected and the objective lens of the camera is adjusted, it is a common practice to remove the whole camera from the patient and to shift it to a position where the eye pupil (almost inside fringe of the iris) can be seen. The vertical and horizontal positions of the camera are adjusted so as to coincide the center of the pupil with the center of the view field, and then the whole camera is slid forward quietly.

In this case, however, when the picture angle becomes as high as about 20° only the eye pupil comes into the field of view and almost all of the fringe portion of the eye pupil is out of the field of view so that it is very difficult to coincide the center of the pupil with the center of the viewing field. According to the present invention, the whole eye pupil including its fringe portion are included in the field of view of the lens system in its wide angle configuration so that it is possible to perform the alignment very easily.

Also according to the present invention, it is possible to reduce the whole length of the optical system by converting the optical system behind the diaphragm into a telecentric optical system within the variable range of magnification.

The present invention can be applied to a non-mydriatic fundus camera in which infrared rays are used as the illumination light beam for observation and a television camera is used in substitution of the eyepiece so as to observe the image through a Braun tube.

What is claimed is:

1. An eye inspecting apparatus comprising:
   an eye inspecting system for inspecting the fundus of an eye to be examined including successively on an optical axis of the eye inspecting apparatus;
   an objective optical member for forming the image of the fundus of the eye to be inspected;
   a diaphragm;
   a movable lens means which moves on the optical axis to cause a change in focal length;
   a telephoto type lens group; and
   an information recording means for recording the image of the fundus of the eye to be examined, said image being formed on an image plane; and
   an illuminating system for illuminating the fundus of the eye to be examined.

2. An apparatus according to claim 1, in which said telephoto type lens group is composed of a front positive sub-group and a rear negative sub-group.

3. An apparatus according to claim 1, in which said eye inspecting system further comprises a fixed lens between said diaphragm and said movable lens means.

4. An apparatus according to claim 3, in which said fixed lens has a cemented surface concave toward said image plane.

5. An apparatus according to claim 1, in which said eye inspecting system further comprises a fixed lens and a movable focusing lens between said diaphragm and said movable lens means.

6. An apparatus according to claim 5, in which said focusing lens is positioned closer to the eye to be inspected than said fixed lens, and has a negative power.

7. An apparatus according to claim 6, in which said second movable lens is positioned closer to said diaphragm than said first movable lens.

8. An apparatus according to claim 7, in which said second movable lens has a larger absolute value focal length than that of said first movable lens.

9. An apparatus according to claim 7, in which said first movable lens has a negative power and said second movable lens has a positive power.

10. An optical inspecting apparatus comprising:
an eye inspecting system comprising:
an objective optical member facing to an eye to be inspected;
a diaphragm, said system having a portion arranged on an image side and a portion arranged on an eye to be inspected side of said diaphragm;
movable lens means for changing the focal length of the eye inspection system being arranged on said image side of the diaphragm and movable along an optical axis of the eye inspecting system,
information recording means for recording information being arranged closer to the image side than the movable lens means and having a photo responsive information recording means movable along the optical axis simultaneously with the movable lens means; and
an illuminating system for illuminating the eye to be examined.

11. An apparatus according to claim 10, in which said movable lens means consists of a movable negative lens and a movable positive lens.

12. An eye inspecting apparatus comprising:
an eye inspecting system for inspecting the fundus of an eye to be inspected comprising:
an objective optical member for forming an image of the fundus of the eye to be inspected;
diaphragm arranged conjugate to the anterior part of the eye to be inspected, said system having a portion arranged on an image side and a portion arranged on an object side of said diaphragm; and
a variable magnification image forming lens group arranged on the image side of said diaphragm and including a first movable lens which moves on an optical axis to cause a change in the focal length of said image forming lens group and a second movable lens which moves on said optical axis independently and simultaneously with said first movable lens;
an illuminating system for illuminating the fundus of the eye to be inspected, said illuminating system having a radiation beam source and beam transmitting member for transmitting beams from said radiation beam source; and
a viewing system coupled to said eye inspecting system for viewing the image formed by said image forming lens group, the image forming lens group being telecentric at its wide angle position of adjustment and non-telecentric at other angles.

13. An apparatus according to claim 12, in which said image forming lens group further comprises a convergent lens at a position closer to the image formed by said image forming lens group than said first and second movable lenses and in which the convergent lens is a telephoto type system.

14. An apparatus according to claim 13, in which the telephoto type system is composed of a positive lens group and a negative lens group in this order from an object.

15. An apparatus according to claim 12, in which the image forming lens group further comprises a correcting lens between said movable lenses and said diaphragm.

16. An apparatus according to claim 15, in which the correcting lens is a double lens composed of a negative lens and a positive lens cemented together.

17. An apparatus according to claim 16, in which the cemented surface of the double lens is concave with respect to said image plane.

18. An apparatus according to claim 12, in which the image forming lens group has a focusing lens arranged closer to the object than the first and second movable lenses.

19. An eye inspecting apparatus comprising:
an eye inspecting system for inspecting the fundus of an eye to be inspected by developing a resultant image of the eye fundus for viewing, said resultant image located furthest from the eye to be inspected than other elements of said system, comprising:
an objective optical member for forming an image of the fundus of an eye to be inspected;
a diaphragm arranged conjugate to the anterior part of the eye to be inspected with respect to said objective member;
a focus lens for focusing the eye inspecting system on the eye fundus, arranged on the image side of said diaphragm;
a fixed lens for compensating aberrations, arranged adjacent to the focusing lens;
a plurality of movable lenses for changing the focal length of the eye inspecting system, arranged on the image side of said focusing lens;
a relay lens for image formation, arranged on the image side of said movable lenses; and
illumination means for illuminating the eye fundus, and a viewing system coupled to said eye inspecting system, for viewing the image of the eye fundus.

20. An eye inspecting apparatus according to claim 19, in which the focusing lens has a negative refractive power, and the fixed lens has a positive refractive power.

21. An eye inspecting apparatus according to claim 20, in which the fixed lens has a cemented surface concave forward the resultant image.

22. An eye inspecting apparatus according to claim 19, in which the relay lens is a telephoto lens.

* * * * *